(12) United States Patent
Jang et al.

(10) Patent No.: US 8,247,230 B2
(45) Date of Patent: Aug. 21, 2012

(54) PLANT STEM CELL LINE DERIVED FROM CAMBIUM OF HERBACEOUS PLANT WITH STORAGE ROOT AND METHOD FOR ISOLATING THE SAME

(75) Inventors: Mi Ok Jang, Jeonju (KR); Eun Kyong Lee, Iksan (KR); Young Woo Jin, Jeonju (KR)

(73) Assignee: Unhwa Corporation (KR)

( * ) Notice: Subject to any disclaimer, the term of this patent is extended or adjusted under 35 U.S.C. 154(b) by 50 days.

(21) Appl. No.: 12/679,269

(22) PCT Filed: Sep. 22, 2008

(86) PCT No.: PCT/KR2008/005605
§ 371 (c)(1),
(2), (4) Date: Mar. 19, 2010

(87) PCT Pub. No.: WO2009/038417
PCT Pub. Date: Mar. 26, 2009

(65) Prior Publication Data
US 2010/0233813 A1    Sep. 16, 2010

(30) Foreign Application Priority Data

Sep. 21, 2007 (KR) .......................... 10-2007-0096893

(51) Int. Cl.
*C12N 5/00* (2006.01)
*C12N 5/02* (2006.01)
(52) U.S. Cl. ........................................ 435/420; 435/410
(58) Field of Classification Search .................. 435/420, 435/410
See application file for complete search history.

(56) References Cited

U.S. PATENT DOCUMENTS

| 5,019,504 | A | 5/1991 | Christen et al. |
| 5,344,775 | A | 9/1994 | Smith |
| 5,407,816 | A | 4/1995 | Bringi et al. |
| 5,550,318 | A | 8/1996 | Adams et al. |
| 5,965,438 | A * | 10/1999 | Kadkade et al. ............ 435/420 |
| 8,017,397 | B2 | 9/2011 | Jin et al. |
| 8,053,238 | B2 | 11/2011 | Jin et al. |
| 2010/0233813 | A1 | 9/2010 | Jang et al. |
| 2010/0255585 | A1 | 10/2010 | Yu et al. |
| 2010/0272692 | A1 | 10/2010 | Park et al. |
| 2011/0033903 | A1 | 2/2011 | Jin |
| 2011/0039312 | A1 | 2/2011 | Jin |
| 2011/0097310 | A1 | 4/2011 | Jang et al. |
| 2011/0117039 | A1 | 5/2011 | Lee et al. |
| 2011/0217273 | A1 | 9/2011 | Hong et al. |
| 2011/0229443 | A1 | 9/2011 | Jin et al. |

FOREIGN PATENT DOCUMENTS

| EP | 1 378 574 A1 | 1/2004 |
| EP | 1 538 214 A1 | 6/2005 |
| EP | 2 399 596 A2 | 12/2011 |
| KR | 1997-0009157 B1 | 6/1997 |
| KR | 1020000056501 A | 9/2000 |
| KR | 10-0290004 B1 | 2/2001 |
| KR | 2001-0094111 A | 10/2001 |
| KR | 2003-0063724 A | 7/2003 |
| KR | 1020030063724 A | 7/2003 |
| KR | 1020040014584 A | 2/2004 |
| KR | 2004-0108052 | 12/2004 |
| KR | 2004/0108052 A | 12/2004 |
| KR | 1020040108052 A | 12/2004 |
| KR | 1020050041259 A | 5/2005 |
| KR | 1020050078372 A | 8/2005 |
| KR | 1020050102571 A | 10/2005 |
| WO | WO 93/017121 A1 | 9/1993 |
| WO | 2007052876 A1 | 5/2007 |
| WO | WO 2009/048306 A1 | 4/2009 |
| WO | WO 2009/139581 A2 | 11/2009 |
| WO | 2009-151302 A2 | 12/2009 |
| WO | 2010-019016 A2 | 2/2010 |
| WO | WO 2010/038991 A2 | 4/2010 |
| WO | WO 2010/095911 A2 | 8/2010 |

OTHER PUBLICATIONS

Teng et al. "Explant preparation affects culture initiation and regeneration of *Panax ginseng* and *Panax quinquefolius*," Plant Cell, Tissue and Organ Culture 68: 233-239, 2002.*

Lancaster et al. "Cell Division and Differentiation in Cambial Explants of Carrot-root Tissue," Aust. J. Plant Physiol., 1985, 12, pp. 47-58.*

Wang et al. "Effect of sorbitol induced osmotic stress on the changes of carbohydrate and free amino acid pools in sweet potato cell suspension cultures," Bot. Bull. Acad. Sin. (1999) 40 219-225.*

Teng et al. "Explant preparation affects culture initiation and regeneration of *Panax ginseng* and *Panax quinquefolius*," Plant Cell, Tissue and Organ Culture 68: pp. 233-239, 2002.*

Wu et al. "Enhancement of saponin production in *Panax ginseng* cell culture osmotic stress and nutrient feeding," Enzyme and Microbial Technology 36 (2005) pp. 133-138.*

(Continued)

*Primary Examiner* — Susan McCormick Ewoldt
(74) *Attorney, Agent, or Firm* — Sterne, Kessler, Goldstein & Fox PLLC (57) ABSTRACT

The present invention relates to a cell line derived from the cambium of an herbaceous plant having a storage root and a method for isolating the same. More specifically, relates to a cambium-derived homogeneous cell line having the ability to divide, which is obtained from the cambium-containing storage tissue of an herbaceous plant having a storage root without a separate dedifferentiation process, and to a method for isolating the same. The cell line derived from the cambium of an herbaceous plant having a storage root has active division ability and is homogeneous. Also, it is stable during culture, because it has not undergone a dedifferentiation process. Thus, through the optimization of proliferation thereof, the cell line can be allowed to proliferate in a large amount within a short time. Accordingly, the cell line derived from the cambium of an herbaceous plant having a storage root makes it possible to produce large amounts of useful plants which are difficult to cultivate outdoor due to various problems associated with the period of cultivation, the selection of cultivation land, cultivation cost and the like.

11 Claims, 6 Drawing Sheets

OTHER PUBLICATIONS

Teng et al., "Explant preparation affects culture initiation and regeneration of *Panax ginseng* and *Panax quinquefolius*," Plant Cell, Tissue and Organ Culture, vol. 68, pp. 233-239 (2002).

Verdeil et al., "Pluripotent versus totipotent plant stem cells: dependence versus autonomy?," Trends in Plant Science, vol. 12(6) pp. 245-252 (Jun. 2007).

Supplementary European Search Report for European Patent Application No. EP 08832692, which is counterpart to PCT/KR2008005605, dated Dec. 2, 2010.

International Search Report for PCT/KR2006/001544, mailed Jun. 28, 2006.

Australian Patent Office Search Report for Application No. SG 201001806-7, mailed Jul. 20, 2010.

Australian Patent Office Written Opinion for Application No. SG 201001806-7, mailed Jul. 20, 2010.

Antoni, H.J. and Folquer, F., "Cultivo "In Vitro" de Tejidos de Batatas *Ipomoea batatas* Lam. Para La Produccion de Nuevos Cultivares," *Revisita Agronomica del Noroeste Argentino* 12(1-2):177-8, Universidad Nacional de Tucuman, Facultad de Agronomia y Zootecnia, Argentina (1975) (Spanish Language).

Asaka, I., et al., "Embryoid Formation by High Temperature Treatment from Multiple Shoots of *Panax ginseng*," Planta Med. 59(4):345-6, George Thieme, United States (Aug. 1993).

Baebler, S., et al., "Establishment of cell suspension cultures of Yew (*Taxus × Media* Rehd.) and assessment of the genomic stability," *In Vitro Cell. Dev. Biol. Plant* 41:338-43, Society for In Vitro Biology, United States (May-Jun. 2005).

Bai, J., et al., "Production of biologically active taxoids by a callus culture of *Taxus cuspidata*," J. Nat. Prod. 67(1):58-63, American Society of Pharmacognosy, United States (Jan. 2004).

Ben Jouira, H., et al., "Adventitious shoot production from strips of stem in the Dutch elm hybrid 'Commelin': plantlet regeneration and neomycin sensitivity," *Plant Cell Tissue and Organ Culture* 53(2):153-60, Klewer Academic Publishers, Netherlands (1998).

Dodds, J.H., and Roberts, L.W., *Experiments in Plant Tissue Culture*, Third Edition, pp. 92-95, Cambridge University Press, England (1999).

Esau, K., *Anatomy of Seed Plants*, Second Edition, pp. 30, John Wiley & Sons, Inc., United States (1977).

Frankenstein, C., et al., "The onset of cambium activity—a matter of agreement?," *Dendrochronologia* (23):57-62, Elsevier GmbH, Italy (2005).

Freeman, S., Biological Science, Second Edition, pp. 823, Pearson Education, Inc., United States (2005).

Gibson, D.M., et al., "Initiation and growth of cell lines of *Taxus brevifolia* (Pacific yew)," Plant Cell Rep. 12(9):479-82, Springer-Verlag, Germany (1993).

Hirasuna, T.J., et al., "Taxol production in suspension cultures of *Taxus baccata*," Plant Cell Tissue and Organ Culture 44(2):95-102, Klewer Academic Publishers, Netherlands (1996).

Kim, M.H., et al., "Growth promotion of *Taxus brevifolia* cell suspension culture using conditional medium," Biotechnol. Bioprocess Eng. 5:350-4, Korean Society for Biotechnology and Bioengineering, Korea (2000).

Kitin, P., et al., "Analysis by Confocal Microscopy of the Structure of Cambium in the Hardwood *Kalopanax pictus*," Annals of Botany 86: 1109-1117, Annals of Botany Company, United States (2000).

Kumar, A., et al., "Morphogenetic responses of cultured cells of cambial origin of a mature tree—*Dalbergia sissoo* Roxb," *Plant Cell Rep.* 9(12):703-706, Springer-Verlag, Germany (1991).

Lachaud, S., et al., "Structure and functions of the vascular cambium," C. R. Acad. Sci. III. 322(8):633-50, Elsevier, France (Aug. 1999).

Lee, E-K., et al., "Cultured cambial meristematic cells as a source of plant natural products," Nat. Biotechnol. 28(11):1213-7, Nature America Publishing, United States (Nov. 2010; Epub Oct. 24, 2010).

Naill, M.C., and Roberts, S.C., "Culture of isolated single cells from *Taxus* suspensions for the propagation of superior cell populations," Biotechnol. Lett. 27(21):1725-30, Kluwer Academic Publishers, Netherlands (Nov. 2005).

Naill, M.C., and Roberts, S.C., "Flow cytometric identification of Paclitaxel-accumulating subpopulations," Biotechnol. Prog. 21(3):978-83, American Institute of Chemical Engineers, United States (May-Jun. 2005).

Naill, M.C., and Roberts, S.C., "Preparation of single cells from aggregated *Taxus* suspension cultures for population analysis," Biotechnol. Bioeng. 86(7):817-26, Wiley, United States (Jun. 2004).

Pyo, S-H., et al. "Efficient purification and morphology characterization of paclitaxel from cell cultures of *Taxus chinensis*," J. Chem. Technol. Biotechnol. 79(10):1162-8, Society of Chemical Industry, England (Oct. 2004, Epub Sep. 3, 2004).

Reynolds, L.B., "Effects of harvest date on some chemical and physical characteristics of American Ginseng (*Panax quinquefolius* L.)," J. Herbs Spices and Medicinal Plants 6(2):63-69, The Haworth Press Inc., United States (1998).

Roberts, S., and Kolewe, M., "Plant natural products from cultured multipotent cells," Nature Biotechnol. 28(11):1175-6, Nature America Publishing, United States (Nov. 2010).

Roberts, S.C., et al. "A simple method for enhancing paclitaxel release from *Taxus canadensis* cell suspension cultures utilizing cell wall digesting enzymes," Plant Cell Rep. 21(12):1217-20, Springer, Germany (Aug. 2003; Epub Jun. 17, 2003).

Strobel, G.A., et al., "Taxol formation in yew—*Taxus*," Plant Sci. 92:1-12, Elsevier Scientific Publishers Ireland Ltd., Ireland (1993).

Wang, C., et al., "Enhanced Taxol Production and Release in *Taxus chinensis* Cell Suspension Cultures with Selected Organic Solvents and Sucrose feeding," Biotechnol. Prog. 17(1):89-94, American Institute of Chemical Engineers, United States (Jan.-Feb. 2001).

Wang, C., et al., "Enhancement of Taxol production and excretion in *Taxus chinensis* cell culture by fungal elicitation and medium renewal," Appl. Microbiol. Biotechnol. 55(4):404-10, Springer International, Germany (May 2001).

West, G., et al., "Cell Cycle Modulation in the Response of thePrimary Root of *Arabidopsis* to Salt Strees," Plant Physiology 135:1050-1058, American Society of Plant Biologists, United States (Jun. 2004).

White, P.R., "Potentially unlimited growth of excised plant callus in an artificial nutrient," American Journal of Botany 26(2):59-64, Botanical Society of America, United States (1939).

Wickremesinhe, E.R.M., and Arteca, R.N., "*Taxus* cell suspension cultures: optimizing growth and production of taxol," J. Plant Physiol. 144:183-8, Urban & Fischer Verlag, Germany (1994).

Woodward, A.W., and Bartel, B., "Auxin: Regulation, Action, and Interaction," Annals of Botany 95: 707-735, Oxford University Press on behalf of the Annals of Botany Company, United States (2005).

Wu, J., and Lin, L., "Enhancement of taxol production and release in *Taxus chinensis* cell cultures by ultrasound, methyl jasmonate and in situ solvent extraction," Appl. Microbiol. Biotechnol. 62(2-3):151-5, Springer Verlag, Germany (Aug. 2003; Epub Mar. 13, 2003).

Ye, Z-H., "Vascular tissue differentiation and pattern formation in plants," Annu. Rev. Plant Biol. 53:183-202, Annual Reviews Inc., United States (2002).

Yokoi, H., et al., "High density cultivation of plant cells in a new aeration-agitation type fermentor," Journal of Fermentation and Bioengineering 75(1):48-52, Society for Biotechnology, Japan (1993).

Yukimune, Y., et al., "Methyl jasmonate-induced overproduction of paclitaxel and baccatin III in *Taxus* cell suspension cultures," Nat. Biotechnol. 14(9):1129-32, Nature America Publishing, United States (Sep. 1996).

Zhang, C.H., et al., "Enhanced paclitaxel production induced by the combination of elicitors in cell suspension cultures of *Taxus chinensis*," Biotechnol. Lett. 22:1561-4, Kluwer Academic Publishers, Netherlands (2000).

Zhong, J.J., "Plant cell culture for production of paclitaxel and other taxanes," J. Biosci. Bioeng. 94(6):591-9, Society for Bioscience and Bioengineering, Japan (2002).

Ziv, M., "Bioreactor technology for plant micropropagation," Hortic. Rev. 24:1-30, John Wiley & Sons, Inc., United States (2000).

English language Abstract of Korean Patent Publication No. KR1997-0009157 B1, European Patent Office, espacenet database—Worldwide, (1997).

English language Abstract Korean Patent Publication No. KR10-0290004 B1, European Patent Office, espacenet database—Worldwide, (2001).

English language Abstract of Korean Patent Publication No. KR 2001-0094111 A, European Patent Office, espacenet database—Worldwide, (2001).

English language Abstract of Korean Patent Publication No. KR 2004-0108052 A, European Patent Office, espacenet database—Worldwide, (2001).

Co-pending Application, U.S. Appl. No. 13/058,949, inventors Jin, et al., filed Aug. 14, 2009.

Office Action from Australian Patent Application No. 2008-202078, Australian Patent Office, dated Aug. 17, 2010.

European Search Report from European Patent Application No. 06757522.5, European Patent Office, Munich, Germany, dated Apr. 22, 2009.

English Language Translation (1 page) of Antoni, H.J. and Folquer, F., "In Vitro Tissue Culture of *Ipomoea batatas* (L.) Lam. Sweet Potato for the Production of New Cultivars," *Revisita Agronomica del Noroeste Argentino 12*:177-8, Universidad Nacional de Tucuman, Facultad de Agronomia y Zootecnia, Argentina (1975).

Restriction/Election Requirement in U.S. Appl. No. 12/889,026, inventors Jin, Y.W., et al., filed on Sep. 23, 2010, mailed on Sep. 19, 2011, U.S. Patent and Trademark Office, Alexandria, VA.

Office Action in U.S. Appl. No. 12/889,026, inventors Jin, Y.W., et al., filed on Sep. 23, 2010, mailed on Dec. 21, 2011, U.S. Patent and Trademark Office, Alexandria, VA.

Restriction/Election Requirement in U.S. Appl. No. 12/889,126, inventors Jin, Y.W., et al., filed on Sep. 23, 2010, mailed on Oct. 28, 2011, U.S. Patent and Trademark Office, Alexandria, VA.

Office Action in U.S. Appl. No. 12/889,126, inventors Jin, Y.W., et al., filed on Sep. 23, 2010, mailed on Dec. 19, 2011, U.S. Patent and Trademark Office, Alexandria, VA.

* cited by examiner

PLANT STEM CELL LINE DERIVED FROM CAMBIUM OF HERBACEOUS PLANT WITH STORAGE ROOT AND METHOD FOR ISOLATING THE SAME

CROSS-REFERENCES TO RELATED APPLICATIONS

This application is a U.S. national phase application, pursuant to 35 U.S.C. §371 of PCT/KR2008/005605, filed Sep. 22, 2008, designating the United States, which claims priority to Korean Application No. 10-2007-0096893, filed Sep. 21, 2007. The entire contents of the aforementioned patent applications are incorporated herein by this reference.

TECHNICAL FIELD

The present invention relates to a cell line derived from the cambium of an herbaceous plant having a storage root and a method for isolating the same, and more particularly to a cambium-derived homogeneous cell line having cell division ability, which is obtained from cambium-containing storage root tissue of an herbaceous plant having a storage root without a separate dedifferentiation process, and to a method for isolating the same.

BACKGROUND ART

*Panax ginseng* C.A. Meyer contains large amounts of useful substances, such as ginsenosides, polyacetylene compounds, polyphenol compounds, polysaccharides containing proteins with host defense functions, polysaccharides having anticomplementary activity, and acidic polysaccharides. However, it is difficult to cultivate and may cause problems associated with pesticide contamination, environmental destruction, etc. In addition, it is very expensive, because it must be cultivated for at least 4 years in order to use the root thereof for medicinal purposes, and thus much manpower and cost are required.

For this reason, studies on methods of using bioengineering methods to produce large amounts of ginseng cells in vitro or to produce ginseng adventitious roots, hairy roots and the like in large amounts have been conducted. It was reported that the growth rate of cell mass (called callus) obtained by culturing ginseng cells in vitro using such cell culture methods is higher than that of ginseng plants obtained in fields (Korean Patent Registration 10-0333559) and that the saponin content of cultured ginseng cells is not significantly lower than that of ginseng roots (Asaka et al., *Plant Med.*, 59:345, 1993).

Accordingly, materials obtained by culturing ginseng adventitious roots (ginseng or true wild ginseng-Korea Forest Service, CBN Biotech, Neobio, KT&G Research Institute, Microplants Bioscience & Biotechnology, etc.) or ginseng cells (Nitto Denko, Japan, etc.) are being used as raw materials for foods and cosmetics (Korean Patent Registration 10-0601903, Korean Patent Registration 10-0637342, Korean Patent Publication 10-2004-0014584). Particularly, true wild ginseng is rare and very expensive, studies focused on culturing the adventitious roots and seedlings thereof to produce ginseng products in large amounts have been actively conducted in various companies and research institutes (Korean Patent Publication 10-2005-0078372).

When culturing herbaceous plants such as ginseng, true wild ginseng and the like, the tissue to be used as a culture material is the root, that is, the storage root. The storage root tissue is a part that is buried in soil for a long period of time to form various relationships with soil microorganisms while absorbing water and inorganic nutrients in the soil during the life thereof. In order to use the storage root tissue in plant cell or tissue culture, sterilization of the tissue is required. However, there are many reports of difficulties in removing microorganisms from the root tissue by surface sterilization because high concentration of sterilizing solution would destroy the tissue and low concentration of the sterilizing solution would cause contamination of the tissue with various fungi and bacteria. This contamination phenomenon becomes severe, particularly in the case of wild-cultivated ginseng and true wild ginseng, which have grown in soil for a long period of time (Korean Patent Registration 10-0478213; Teng, W. L. et al., *Plant Cell Tissue Organ Cult.*, 68:233, 2002).

Also, in order to produce large amounts of cells of ginseng storage root among plant storage tissues, the ginseng tissue must undergo a process for dedifferentiation of the storage root (differentiated tissue) into undifferentiated tissue, in any kind of production method among currently known methods. In this process, the somaclonal variation may unavoidably occur. In other words, in order to produce the cells of ginsengs in large amounts using plant tissue culture techniques, a genetically stable sample must be used as a material in order to reduce somaclonal variation. It was reported in Korean Patent Publication 10-2005-0078372 that somaclonal variation basically occurs even if any tissue of ginsengs is used.

Meanwhile, cambium is a tissue that thickens the stem and root to allow the plant grow volumetrically. It was reported that when the cambium, a meristem where the most active cell division occurs, is used as an explant for plant cell tissue culture, rapid and mass production of cells is possible (Korean Patent Registration 10-0533120). Studies on structure and ultrastructure of this cambium have progressed slowly because of inherent technical difficulty in using the material. It was reported that, because the cambium is composed of several narrow, elongated and thin-walled cell layers, it is easily damaged during extraction. Also, it was reported that highly vacuolated active meristematic cells are difficult to fix even either by a conventional method employing an electron microscope or by techniques recently developed in order to study the in situ localization of proteins, RNAs and other molecules (Lachaud Suzanne et al., *Life Science*, 633, 1999).

In addition, the mechanical sectioning of the continuous cambium was not widely used, and this is believed to be because of the technical difficulties of isolating cambium cells that have long length and are thin-walled. In many studies, it was reported that the shape, size and arrangement of cambium cells were characterized indirectly based on the structure of cambium derivatives on the assumption that the structure of the secondary vascular tissue reflects the cambium (Kitin, P. et al., *Ann. Bot.*, 86:1109, 2000). In other words, several studies suggest that there is much difficulty in using cambium directly as a material for studies in various fields.

Korean Patent Registration 10-0533120 developed by some of the present inventors discloses a method of inducing callus using the cambium collected from the stem of a plant. This registered patent relates to a plant cell culture method for obtaining plant cells rapidly in large amounts and mentions a plant cell culture method of inducing callus through the cambium collected from the plant stem rather than using a general seed culture method. The registered patent suggests a method of inducing cambium cells by using the cambium of woody plant stem with addition of high concentrations of auxin picloram and gibberellic acid, but in this registered patent, the callus is merely induced from the cambium of woody plant stem. Because the callus is a tissue formed through a dedifferentiation process, this registered patent still has the problem of variation caused by dedifferentiation.

Furthermore, some of the present inventors developed the invention of PCT/KR 2006/001544, which solves the problem of variation caused by dedifferentiation and relates to a method for providing cell lines that can stably proliferate and have high genetic stability. The method disclosed in the PCT application also uses the cambium of woody plant stem, but because morphological and physiological characteristics of herbaceous plants such as ginseng plants are different from those of woody plants, there has been a need to develop an improved invention which considers the characteristics of herbaceous plants in order to induce cell lines from the cambium of storage root tissue of herbaceous plants.

Accordingly, the present inventors have made extensive efforts to obtain a plant cell line, which is a homogeneous cell line having the ability to divide, and has not undergone a dedifferentiation process, and thus has no somaclonal variation during culture. As a result, the present inventors have isolated a cambium-derived cell line by applying osmotic stress to cambium-containing storage root tissue and culturing the storage root tissue in a specific plant hormone-containing medium, and have found that the isolated cell line is a homogeneous cell line, which has an unlimited ability to divide, has been isolated without a dedifferentiation process to have no somaclonal variation, and thus is genetically highly stable and physiologically uniform, thereby completing the present invention.

SUMMARY OF INVENTION

It is an object of the present invention to provide a cell line derived from the cambium of herbaceous plant storage roots, which has the ability to divide, is homogeneous and can stably proliferate during culture.

Another object of the present invention is to provide a method of isolating said cell line without a dedifferentiation process.

To achieve the above object, in one aspect, the present invention provides a method for isolating a cell line derived from the cambium of an herbaceous plant having a storage root, the method comprising the steps of
 (a) obtaining storage root tissue containing the cambium of an herbaceous plant having a storage root;
 (b) inducing a cambium-derived cell line by culturing the obtained cambium-containing storage root tissue in a medium containing IAA (indole-3-acetic acid) or IBA (indole-3-butyric acid), wherein osmotic stress is applied to the cambium-containing storage root tissue during, before or after the culture; and
 (c) collecting the induced cambium-derived cell line.

In another aspect, the present invention provides a cell line, which is derived from the cambium of an herbaceous plant having a storage root and has the following characteristics:
 (a) it is in an innately undifferentiated state;
 (b) it is a homogeneous cell line; and
 (c) it is morphologically characterized by numerous vacuoles.

In still another object, the present invention provides a method for preserving an herbaceous plant cell line, comprising freezing a cell line derived from the cambium of an herbaceous plant having a storage root.

Other features and aspects of the present invention will be apparent from the following detailed description and the appended claims.

BRIEF DESCRIPTION OF DRAWINGS

The patent or application file contains at least one drawing executed in color. Copies of this patent or patent application publication with color drawing(s) will be provided by the Office upon request and payment of the necessary fee.

In FIG. 10, ginseng wet cell, ginseng dry cell, ginseng cell-cultured medium, E1: elicitation 1 stage, E2: elicitation 2 stage, G: growth stage, and RA: retinoic acid.

In FIG. 11, ginseng wet cell, ginseng dry cell, ginseng cell-cultured medium, E1: elicitation 1 stage, E2: elicitation 2 stage, G: growth stage).

DETAILED DESCRIPTION OF THE INVENTION AND PREFERRED EMBODIMENTS

Unless otherwise defined, all technical and scientific terms used herein have the same meaning as commonly understood by one of ordinary skill in the art. Generally, the definitions of various terms used herein are well known and conventionally used in the art.

In one aspect, the present invention relates to a method for isolating a cell line derived from the cambium of an herbaceous plant having a storage root.

When leaves, stems or roots that are already differentiated tissues are used, they must undergo a dedifferentiation process in which a differentiated tissue rejuvenates to an undifferentiated tissue, in order to form a callus. In the dedifferentiation process, a somaclonal variation occurs, leading to cell instability. While, the present inventors have conducted studies on a plant cell system having little or no somaclonal variations. As a result, the present inventors have found that, when a cell line is specifically induced only in cambium that is meristem, the active cell division ability of the meristem itself can be used without dedifferentiation, such that a somaclonal variation does not occur, and thus a genetically highly stable and physiologically uniform homogeneous cell line can be induced. On the basis of this finding, the present inventors have isolated a cambium-derived cell line.

The isolation method according to the present invention comprises the steps of: (a) obtaining storage root tissue containing the cambium of an herbaceous plant having a storage root; (b) inducing a cambium-derived cell line by culturing the obtained cambium-containing storage root tissue in a medium containing IAA (indole-3-acetic acid) or IBA (indole-3-butyric acid), wherein osmotic stress is applied to the cambium-containing storage root tissue during, before or after the culture; and (c) collecting the induced cambium-derived cell line.

In step (b) of the inventive method, the application of osmotic stress is carried out in order to induce the cell line specifically in the cambium. Preferably, it is carried out before culturing the tissue in the IAA- or IBA-containing medium, such that general tissues (i.e., cortex, phloem, xylem and pith) other than the cambium lose the ability to divide, and thus become necrotic when they are treated with a cambial division-specific hormone such as IAA or IBA.

Preferably, step (c) is carried out by proliferating the induced cambium-derived cell line in a medium containing one or more of 2,4-D (2,4-dichlorophenoxyacetic acid, picloram and IBA, and then collecting the cambium-derived cell line.

The method according to the present invention will now be described in detail.

(1) Sterilization Process and Process of Treatment with Osmotic Stress

First, the cambium-containing storage root tissue of an herbaceous plant is prepared, and then subjected to a sterilization process. Herein, the sterilization process is carried out in two steps. Then, the cambium-containing storage root tissue subjected to the sterilization process is treated with osmotic stress, such that general tissues (i.e., cortex, phloem, xylem and pith) other than the cambium lose division ability in an extreme environment, and thus become necrotic when treated with a cambium division-specific hormone such as IAA or IBA, and a homogeneous cell line having the ability to divide is specifically induced only in the cambium having an active cell division ability. Herein, sugars such as sucrose, sugar alcohols such as sorbitol, and salts such as sodium chloride may be used as the osmotic agents, but are not limited thereto.

Herein, preferably, the osmotic agent is used in an amount of 0.5-2M, and the osmotic stress is applied in a cold state or at room temperature for 16-24 hours, and then removed. However, the scope of the present invention is not limited thereto, because the concentration, treatment time and temperature of the osmotic agent may vary depending on the kind of plant and the state of tissue.

Meanwhile, the present invention is characterized in that, after treatment with the osmotic stress, a step of removing the osmotic stress and a step of cell adaptation to induction medium are carried out. In order to release the osmotic stress, the concentration of the osmotic agent is reduced rapidly to, for example, 0.03-0.05M, and then it is treated to the explant. Herein, the treatment time is preferably 1-15 minutes. Also, if the explant is continuously exposed to the above-described low concentration of the osmotic agent, the low concentration of the osmotic agent differs from that of a medium inducing the cambium-specific cell line, and this difference can also act as osmotic stress during culture. For this reason, a step of adapting the explants to the induction medium is preferably further carried out. The step of adapting the explant to the induction medium is carried out by treating the explant, subjected to the osmotic stress removal step, with an osmotic agent at a concentration similar to that of the induction medium. Herein, the explant is preferably treated with the osmotic agent at a concentration of 0.08-0.1M for 1-15 minutes.

In one Example of the present invention, the case treated with osmotic stress was compared with a control group not treated with osmotic stress. Herein, the induction of a cambium-specific cell line did not appear in the control group not treated with osmotic stress, suggesting that the step of treatment with osmotic stress is necessary to induce a cell line derived from the cambium of an herbaceous plant having a storage root.

(2) Induction of Cell Line Derived from Cambium of Herbaceous Plant Having Storage Root After treatment with the osmotic stress, in order to induce a cell line derived from the cambium of an herbaceous plant, the tissue which has undergone the osmotic stress is placed in a cell culture medium containing IAA or IBA, such that cell division is specifically induced only in the cambium, thus obtaining a cambium-derived homogeneous cell line. Preferably, the cambium-containing explants is placed in a medium containing 0.5-3.0 mg/L of IAA or IBA.

If IAA is added to the cell line induction medium, it combines with endogenous IAA contained in the plant to induce a synergistic effect on the cambial activity. As a result of such a synergistic effect, a homogeneous cell line is specifically induced only in the cambium due to the difference in cell division activity between differentiated tissue and meristem that is the cambium. Meanwhile, it was reported that IAA is the primary natural auxin, whereas IBA is the secondary natural auxin (Andrew et al., *Ann. Bot.*, 95:707, 2005).

In one Example of the present invention, after treatment with osmotic stress, the explant was treated with other plant hormone auxins, such as picloram, 2,4-D, CPA and NAA. However, it was shown that only IAA and IBA were effective in inducing a cell line derived from the cambium of an herbaceous plant having a storage root.

(3) Proliferation of Cell Line Derived from Cambium of Herbaceous Plant Having Storage Root The cambium-derived homogeneous cell line induced as described above may be transferred into an optimal growth medium containing the plant growth regulator auxin in order to obtain the homogeneous cell line in a large amount. Herein, as the growth regulator, one or more of 2,4-D (2,4-dichlorophenoxyacetic acid), picloram and IBA are preferably used. Any one of 2,4-D, picloram and IBA is preferably used in an amount of 1-5 mg/L, and more preferably 2 mg/L.

The medium used in the present invention is a conventional medium for plant tissue culture, and examples thereof may include, but are not limited to, N6 medium, SH medium, MS medium, AA medium, LS medium, B5 medium, WPM medium, LP medium, White medium, GD medium, DKW medium, DCR medium, etc.

In another aspect, the present invention relates to a cell line, which is derived from the cambium of an herbaceous plant having a storage root and has the following characteristics:
 (a) it is in an innately undifferentiated state;
 (b) it is a homogeneous cell line; and
 (c) it is morphologically characterized by numerous vacuoles.

The cambium-derived cell line according to the present invention is additionally characterized in that: (a) it is present as single cells during suspension culture; (b) it has low sensitivity to shear stress in a bioreactor compared to cell lines derived from tissues other than the cambium of an herbaceous plant having a storage root; and (c) it has high growth rate and is stably cultured compared to cell lines derived from tissues other than the cambium of an herbaceous plant having a storage root.

In one Example of the present invention, it was seen that the cambium-derived cell line according to the present invention could be cultured in large scale not only in a 3 L bioreactor, but also in a 20 L bioreactor. Also, it was seen that the cambium-derived cell line according to the present invention had 5-9-fold lower sensitivity to shear stress compared to cell lines derived from tissues other than cambium and had 3-5-fold higher growth rate compared to cell lines derived from tissues other than cambium. Meanwhile, when the cambium-derived cell line was cultured for 11 months or more, it showed growth rate difference of a maximum of 400 fold from cell lines derived from tissues other than cambium.

In another Example of the present invention, cell line extract and culture medium according to the present invention had the effect of inhibiting the expression of MMP-1 that degrades skin collagen to form skin wrinkles, thus suggesting that they have the effect of preventing and reducing wrinkles. In still another Example of the present invention, it was confirmed that the cell line extract and culture medium had the effect of inhibiting reactive oxygen induced by UV, thus suggesting that they have antioxidative effect.

In still another object, the present invention relates to a method for preserving an herbaceous plant cell line, comprising freezing a cell line derived from the cambium of an herbaceous plant having a storage root.

In one Example of the present invention, cryopreservation tests were carried out for a ginseng cotyledon-derived heterogeneous cell line and a ginseng cambium-derived homogeneous cell line. As a result, it was seen that the ginseng cotyledon-derived heterogeneous cell line did not regrow when thawed, whereas ginseng cambium-derived homogeneous cell line started to regrow and proliferate when thawed.

If cell lines can be cryopreserved, it is possible to stably supply raw materials and construct a substantial master cell line bank. Thus, the inventive cell line derived from the cambium of an herbaceous plant having a storage root enables a long-term and stable supply of an herbaceous plant cell line.

The world is now at war for securing research materials (biological resources), and the preservation and identification of biological resources for developing various new drugs and improving food quality, including human tissue, plant seeds, microorganisms, cells and genes, have become important national properties. Accordingly, because securing research materials leads to national competitiveness, it is required to construct cell line banks for developing, collecting, preserving and distributing cell lines, which are used as essential materials in studies in the bioscience-related field. Thus, when such plant cell line banks are constructed, the supply of research materials can become smooth, and the period of studies employing plant cell lines can be shortened.

The present invention is characterized by using the cambium of a storage root and can be applied to all kinds of herbaceous plants having general storage roots. In other words, in one Example of the present invention, cell lines were isolated from the cambiums of ginseng, true wild ginseng and carrot storage roots, but it will be obvious to those skilled in the art that the method of the present invention can be applied to any herbaceous plant, as long as the herbaceous plant has a storage root. Examples of herbaceous plants having storage roots include, but are not limited to, *Codonopsis lanceolata, Ostericum koreanum* KITAGAWA, *Platycodon grandiflorum, Pueraria thunbergiaana, Aralia contonentalis* Kitagawa, Ledebouriella seseloides, *Angelica gigas* NAKAI, carrot, sweet potato, Maca, cassava, ginseng, true wild ginseng, wild-cultivated ginseng, etc. Also, the inventive cambium-containing storage tissue of an herbaceous plant having a storage root is meant to include not only the storage root tissue of outdoor plants, but also tissue cultures (adventitious roots and adventitious root-derived cell lines).

EXAMPLES

Hereinafter, the present invention will be described in further detail with reference to examples. It will be obvious to those skilled in the art that these examples are illustrative purpose only and are not to be construed to limit the scope of the present invention, because these examples can be modified into other various forms.

Example 1

Figure 1:
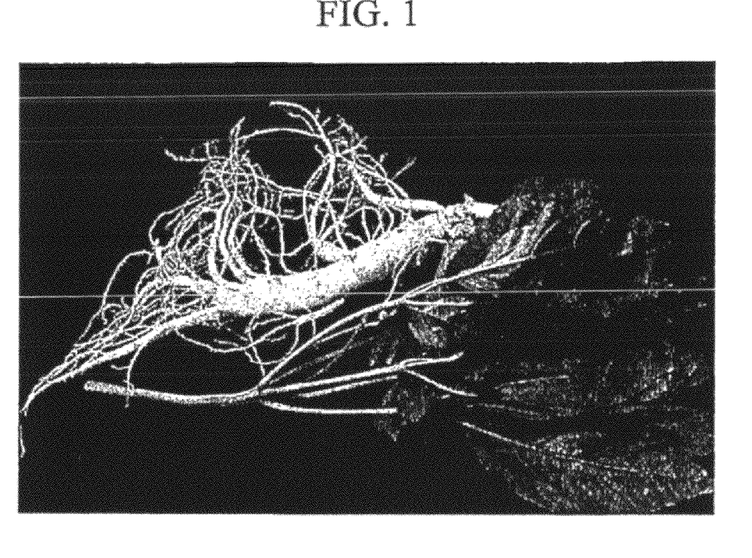
FIG. 1 shows the typical feature of an outdoor-cultivated ginseng used in the present invention.

Isolation of Cell Line Derived from Cambium of Herbaceous Plant Having Storage Root: (1)-Ginseng 1-1: Preparation of Plant Material FIG. 1 shows the typical feature of an outdoor-cultivated ginseng used in the present invention. As shown in FIG. 1, only ginseng, which was smooth and had no wound, was selected and collected. The collected ginseng was washed under running tap water to remove soil or other contaminants from the outer surface of the ginseng. Then, the fine roots of the ginseng were all removed to leave only the main root, and the surface of the main root was washed with a liquid detergent, and then the main root was left to stand under running tap water. The washed tissue was placed in a sterilized flask in a clean bench and sterilized with 70% ethanol for about 30 seconds to 1 minute. Then, the tissue was rinsed with sterile distilled water, and then disinfected with 1-1.5% sodium hypochlorite (Junsei, Japan) for 5-8 minutes. Then, the disinfectant solution was discarded, and the tissue was rinsed one or more times with sterile distilled water, and then secondarily treated with the disinfectant solution for about 5-8 minutes. Herein, in order for the disinfectant solution to penetrate into the tissue, several drops of TWEEN 20 (polyoxyethylenesorbitan monolaurate (Junsei, Japan) were added to the disinfectant solution, and then the treated tissue was rinsed 3-5 times with sterile distilled water. Then, in order to prevent the browning of the sterilized tissue, the sterilized main root was placed in BIM (browning inhibition medium) containing an antioxidant, and shake-cultured for about 30 minutes to 1 hour. Then, moisture was removed from the tissue using sterilized filter paper.

TABLE 1

Composition and concentration of BIM (salt was added in an amount corresponding to ¼ of the total concentration)

| Component | Concentration |
|---|---|
| McCown WPM salt | ¼ strength |
| Sucrose | 1% (w/v) |
| PVP(polyvinyl pyrrolidone) | 0.5% (w/v) |
| Ascorbic acid | 100 mg/l |
| Citric acid | 150 mg/l |

Adjust to pH 5.8

Figure 2:
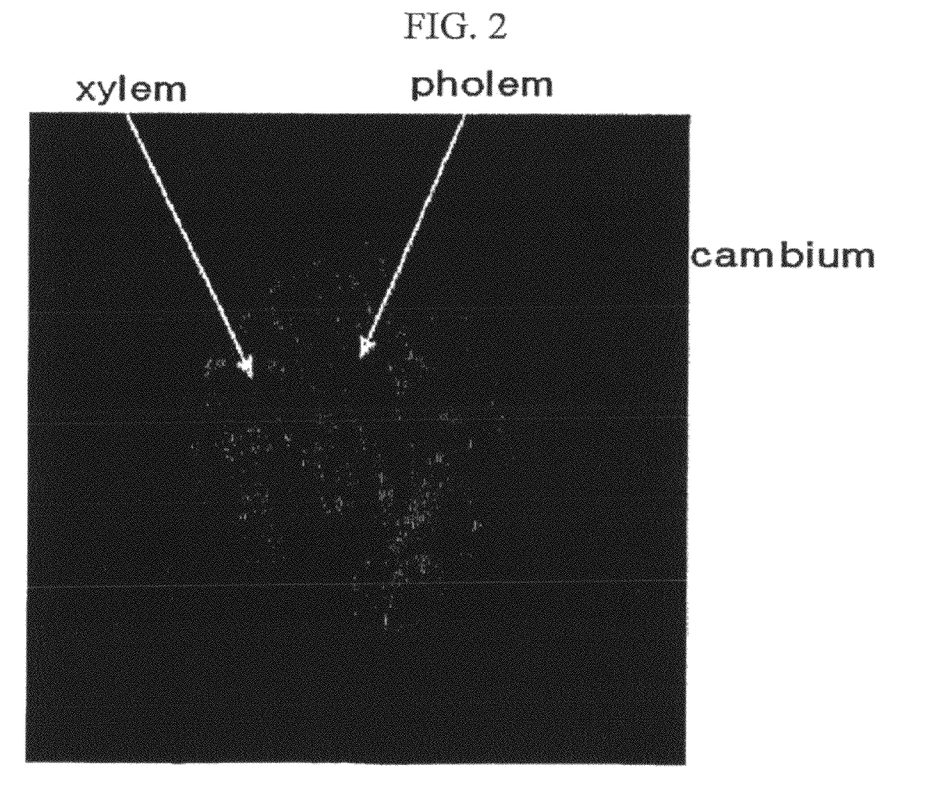
FIG. 2 shows the feature of a prepared explant containing the cambium of a ginseng storage root among plant storage tissues.

Then, in order to prevent the browning of the material, the main root was placed on a sterilized dish containing an antioxidant-containing CS solution (cutting solution) shown in Table 2 below, and the main root was peeled thinly and cut into two pieces. The cut parts were sliced to a size of 0.5-0.7 cm (width)×0.5-0.7 cm (length)×0.2-0.5 mm (height), such that the cambium having an active cell division ability was included in the cut parts. FIG. 2 shows a cambium-containing explant prepared by cutting the ginseng storage root to the above-specified size.

TABLE 2

CS (cutting solution)

| Component | Concentration |
|---|---|
| PVP(Polyvinyl pyrrolidone) | 0.5% (w/v) |
| Ascorbic acid | 100 mg/l |
| Citric acid | 150 mg/l |

1-2: Treatment of Ginseng Main Root Cambium-Containing Explant with Osmotic Agent The explant prepared in Example 1-1 was treated with osmotic stress in order to necrotize differentiated tissues (phloem, xylem, pith, etc.) and induce only the cambium (meristem). The cambium-containing explant was blotted onto a preinoculation medium (medium 1) having filter paper laid thereon, and it was placed in a flask containing 1M sucrose solution (Duchefa, Netherland) and treated with osmotic stress in a cold state for 16-24 hours. Then, the explant was treated in 0.05M sucrose solution for 5 minutes and in 0.1M sucrose solution for 5 minutes to remove the stress caused by the high-concentration sucrose. The cambium-containing explant from which the osmotic stress has been removed was placed on a preinoculation medium (medium 1) having filter paper laid thereon to remove moisture.

TABLE 3

Preculture medium (medium 1)

| | composition | mM | mg/l |
|---|---|---|---|
| Macroelements | Ca(NO₃)₂ | 2.35 | 471.26 |
| | NH₄NO₃ | 5 | 400 |
| | MgSO₄•7H₂O | 1.5 | 180.54 |
| | K₂SO₄ | 5.68 | 990 |
| | CaCl₂•2H₂O | 0.65 | 72.5 |
| | KH₂PO₄ | 1.25 | 170 |

TABLE 3-continued

Preculture medium (medium 1)

| | composition | µM | mg/l |
|---|---|---|---|
| Microelements | MnSO₄•4H₂O | 131.94 | 22.3 |
| | ZnSO₄•7H₂O | 29.91 | 8.6 |
| | Na₂MoO₄•2H₂O | 1.03 | 0.25 |
| | H₃BO₃ | 100.27 | 6.2 |
| | CuSO₄•5H₂O | 1.0 | 0.25 |
| | FeNa-EDTA | 100 | 36.7 |
| Vitamin | Glycine | 26.64 | 2.0 |
| | myo-Inositol | 554.94 | 100 |
| | Nicotinic acid | 4.06 | 0.5 |
| | Pyridoxine-HCl | 2.43 | 0.5 |
| | Thiamine-HCl | 2.96 | 1.0 |

1-3: Induction of Cambium-Derived Homogeneous Cell Line in Explant Containing Cambium of Main Root of Ginseng In order to induce a cambium-derived homogeneous cell line having the cell division ability, the explant treated with osmotic stress in Example 1-2 was transferred to a cell line induction medium (medium 2). The composition of the medium used is shown in Table 4 below. The transferred explant was cultured in a dark condition at 22±1° C.

TABLE 4

Medium (medium 2) composition to induce a cambium-derived homogeneous cell line

| Component | Concentration and condition |
|---|---|
| Salt | Full strength WPM |
| Sucrose | 3% (w/v) |
| IAA(Indole-3-acetic acid) | 2 mg/l |
| pH | 5.8 |
| Gelrite | 0.3% (w/v) |
| Ascorbic acid | 100 mg/l |
| Citric acid | 150 mg/l |

Figure 3:
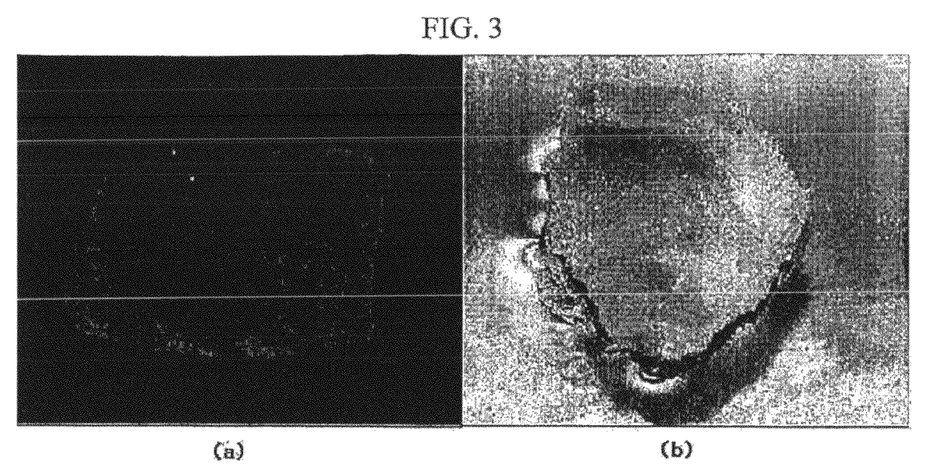
FIG. 3(a) shows that a homogeneous cell line having the ability to divide was induced specifically in the cambium of an explant containing the cambium of a ginseng root.
FIG. 3(b) shows that cells were induced throughout the cross section of an explant, when a general culture system was used.

After the osmotic stress was treated and removed as described above, it was observed that, from the explant inoculated onto the cambium-derived cell line induction medium (medium 2), a homogeneous cell line was specifically induced only in the cambium without being induced in other tissues. This observation is shown in Table 5 below. Specifically, it was observed that, in the transferred explant which has been treated with osmotic stress and from which the osmotic stress has been released, the cambium of the explant started to turn a light yellow after 3-7 days of the culture, and after about 7-14 days therefrom, a round cell line was induced at the portion changed to the light yellow color. FIG. 3(a) shows that the homogeneous cell line was specifically induced only in the cambium of the ginseng root cambium-containing explant.

However, as shown in Table 5 below, in the explants transferred directly onto the cambium-derived cell line induction medium (medium 2) without carrying out the osmotic stress-treating step of Example 1-2, a yellow color reaction was shown with respect to the cambium at an initial stage (2-3 days) after the transfer, and then with the passage of time, the entire explant turned yellow. The explant which has showed the yellow color reaction with respect to the cambium was subcultured in an optimal medium (medium 3) for the isolation and proliferation of a cambium-derived cell line in order to induce and proliferate the cambium-derived cell line, but the browning phenomenon became severe, and any reaction other than the browning color reaction was not shown even with the passage of time. This suggests that the step of treatment with osmotic stress is necessary to induce the cambium-derived cell line.

TABLE 5

Comparison of reaction between explant treated with osmotic stress and explant not treated with osmotic stress

| Treatment | Not treated | Treated for 16 hours | Treated for 20 hours | Treated for 24 hours |
|---|---|---|---|---|
| Aspect | A yellow color reaction progressed with respect to the cambium at the initial stage after the inoculation, while this reaction spread throughout the explant. Then, a severe browning color reaction progressed throughout the explant including the cambium, and the induction of a homogeneous cell line, specific in the cambium, was no longer shown. | It was observed that cells were specifically induced only in the cambium. When the explant was treated with osmotic stress for varying periods of time, similar results were shown. In other words, there was no significant difference in reaction between the treatment periods. | | |

Meanwhile, in order to examine the influence of the hormone used in the induction medium, the explant was cultured in a 2,4-D-containing medium, which was not the cambium-derived cell line induction medium and has been used in the conventional culture of general ginsengs. In this case, it was observed that the entire explant started to turn yellow after 7-10 days of the culture, and about 7-14 days therefrom, cells were induced throughout the whole cross section (FIG. 3(b)). In other words, it could be seen that, when 2,4-D was used, cell line was induced all other tissues, non-specifically to the cambium.

As shown in FIG. 3(b), when a general culture system containing 2,4-D was used in culture, cells were induced from various tissues (cortex, phloem, xylem, cambium, pith, etc.) present in the entire cross section, and the various cells were mixed with each other. Thus, the induced and proliferated cells had heterogeneity. However, as shown in FIG. 3(a), when the inventive method comprising treating the explant with osmotic stress, releasing the osmotic stress and transferring the explant into the cambium-derived cell line induction medium was used, cells were specifically induced only from the cambium, and thus consisted only of cambium cells. Thus, the induced cells had homogeneity.

1-4: Proliferation of Cambium-Derived Homogeneous Cell Line in Explant Containing Cambium of Main Root of Ginseng As shown in FIG. 3(a), after the explant was cultured in medium 2 of Example 1 to necrotize tissues other than the cambium, it was subcultured in medium 3. Medium 3 is an optimal medium for the proliferation of the cambium-derived cell line and is based on the basal salt composition shown in Table 6. It is shown in Table 7.

TABLE 6

Basal salt composition of optimal medium for the proliferation of the cambium-derived cell line

| | Composition | mM | mg/L |
|---|---|---|---|
| Macroelements | $CaCl_2 \cdot 2H_2O$ | 2.99 | 332.02 |
| | $KH_2PO_4$ | 1.25 | 170 |
| | $KNO_3$ | 18.79 | 1900 |
| | $MgSO_4$ | 1.5 | 180.54 |
| | $NH_4NO_3$ | 20.61 | 1650 |

| | Composition | uM | mg/L |
|---|---|---|---|
| Microelements | $CoCl_2 \cdot 6H_2O$ | 0.11 | 0.025 |
| | $CuSO_4 \cdot 5H_2O$ | 0.1 | 0.025 |
| | FeNa-EDTA | 100 | 36.7 |
| | $H_3BO_3$ | 100.27 | 6.2 |

TABLE 6-continued

Basal salt composition of optimal medium for the proliferation of the cambium-derived cell line

| | | | |
|---|---|---|---|
| | KI | 5.0 | 0.83 |
| | $MnSO_4 \cdot 4H_2O$ | 100 | 16.9 |
| | $Na_2MoO_4 \cdot 2H_2O$ | 1.03 | 0.25 |
| | $ZnSO_4 \cdot 7H_2O$ | 29.91 | 8.6 |
| Vitamins | Glycine | 26.64 | 2.0 |
| | myo-Inositol | 554.94 | 100 |
| | Nicotinic acid | 4.06 | 0.5 |
| | Pyridoxine-HCl | 2.43 | 0.5 |
| | Thiamine-HCl | 0.3 | 0.1 |

TABLE 7

Optimal medium (medium 3) composition for the proliferation of the cambium-derived cell line

| Component | Concentration and condition |
|---|---|
| Salt | Full strength MS |
| Sucrose | 3% (w/v) |
| 2,4-D(2,4-dichlorophenoxyacetic acid) | 2 mg/L |
| pH | 5.8 |
| Gelrite | 0.3% (w/v) |
| Ascorbic acid | 100 mg/L |
| Citric acid | 150 mg/L |

Figure 4:
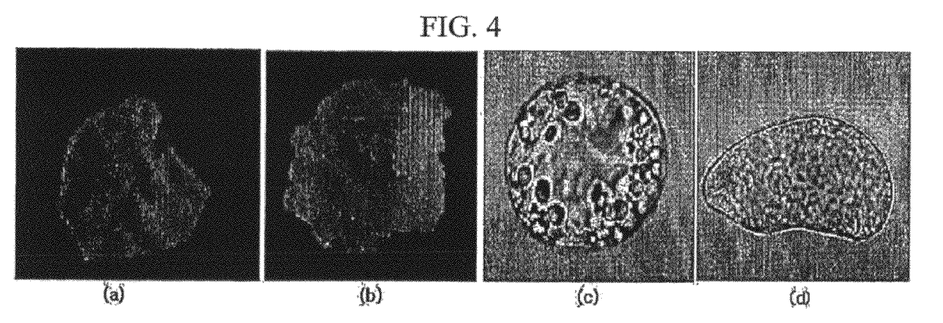
FIG. 4(a) shows that a cell line derived from the cambium of a ginseng root was induced, isolated and allowed to proliferate in a growth medium, which is before it was isolated from the medium.
FIG. 4(b) shows that the cambium-derived cell line was isolated and allowed to proliferate in a large amount.
FIG. 4(c) shows that the cambium-derived cell line was observed under an optical microscope at the single-cell level.
FIG. 4(d) shows that a ginseng cotyledon-derived callus (KCTC 10224) was observed under an optical microscope at the single-cell level.

FIG. 4(a) shows that the homogeneous cell line induced specifically in the cambium of the cambium-containing explants transferred onto medium 2 was subcultured and proliferated in medium 3 shown in Table 7.

When the cambium-derived homogeneous cell line having the ability to divide was cultured in medium 3, it continually divided and proliferated. After about 10-20 days of the culture, the cambium-derived cell line was isolated, and the isolated cell line was allowed to proliferate again in the same medium (medium 3).

FIG. 4(b) shows that the isolated cambium-derived cell line was allowed to proliferate in medium 3 shown in Table 7. Meanwhile, if the cell line was cultured in a growth medium containing IAA, not 2,4-D, it did not proliferate and showed a tendency to differentiate, suggesting that IAA cannot be used in growth medium. FIG. 4(c) shows that the cambium-derived homogeneous cell line was observed under an optical microscope at the single-cell level, and FIG. 4(d) shows that a ginseng cotyledon-derived callus (KCTC 10224) was observed under an optical microscope at the single-cell level.

Example 2

Induction and Proliferation of Cell Line Derived from Cambium of Herbaceous Plant Having Storage Root: (2)-True Wild Ginseng 2-1: Induction of Cell Line Derived from Cambium of True Wild Ginseng True wild ginseng was prepared and surface-sterilized in the same manner as in Example 1-1. Also, a 100-year-old true wild ginseng adventitious root maintained in a bioreactor was prepared and placed in a sterilized dish containing the CS solution of Table 2, and a cambium-containing explant was obtained from the true wild ginseng in the same manner as described above. Then, the two prepared samples were treated with osmotic stress in the same manner as in Example 1-2 and Example 1-3, and then homogeneous cell lines derived from the cambiums were induced.

Figure 5:
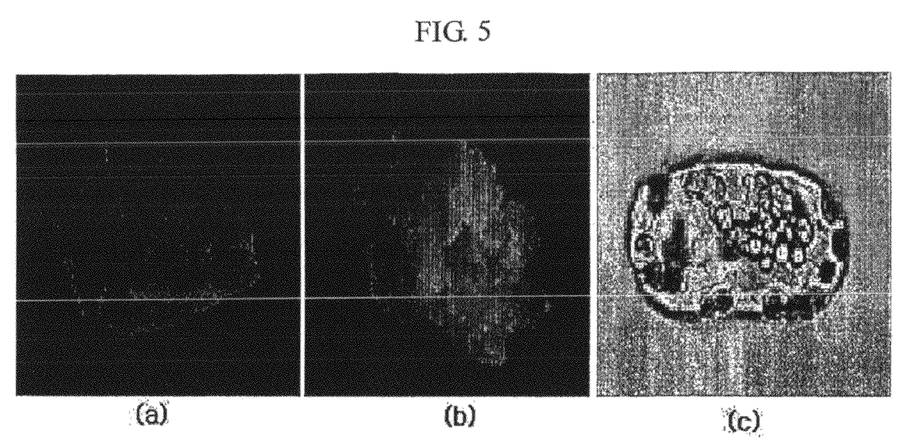
FIG. 5(a) shows that a homogeneous cell line having the ability to divide was induced specifically in the cambium of a true wild ginseng cambium-containing explant.
FIG. 5(b) shows that a cambium-derived cell line was isolated and allowed to proliferate in a large amount.
FIG. 5(c) shows an optical microscopy of a cambium-derived cell line at a single cell level.

As a result, it was observed that, in both the true wild ginseng cambium-containing explant and the true wild ginseng adventitious root cambium-containing explant, which have been treated with osmotic stress, osmotic stress-removed and transferred to the homogeneous cell line induction medium in the same manner as in Example 1 employing ginseng, cells were specifically induced only from the cambiums without being induced in other tissues. FIG. 5(a) shows the induction of the homogeneous cell line having the ability to divide specifically in the cambium of the explant containing the cambium of the true wild ginseng was induced.

2-2: Proliferation of Cell Line Derived from Cambium of True Wild Ginseng

As shown in FIG. 5(a), after the homogeneous cell line was specifically induced only in the cambium using osmotic stress treatment and medium 2, the homogeneous cell line induced in the explant containing the cambium of true wild ginseng was subcultured in medium 3 of Table 7 in the same manner as in Example 2. As a result, the cambium-derived homogeneous cell line having the ability to divide continually divided and proliferated, and thus after about 10-20 days of the culture, the cambium-derived homogeneous cell line having the ability to divide could be isolated. The true wild ginseng cambium-derived homogeneous cell line thus isolated was allowed to proliferate again by culturing it in the same medium. FIG. 5(b) shows that the isolated cambium-specific homogeneous cell line was allowed to proliferate in medium 3 shown in Table 7. Also, FIG. 5(c) shows that the true wild ginseng cambium-derived homogeneous cell line was observed under an optical microscope at the single-cell level.

Meanwhile, in the true wild ginseng adventitious root cambium-containing explant in Example 2-1, the cell line was allowed to proliferate in the same manner as in Example 2, except that IBA was used instead of 2,4-D in Table 7. As a result, when the cell line was cultured in the IAA-containing medium, it did not differentiate and showed a tendency to differentiate, whereas, when the cell line was cultured in the IBA-containing medium, it did not differentiate and proliferated in the same manner as in the case where the 2,4-D-containing medium was used.

Example 3

Induction and Proliferation of Cell Line Derived from Cambium of Herbaceous Plant Having Storage Root: (3)-Carrot A carrot (*Daucus carota* L.) was prepared and surface-sterilized in the same manner as in Example 1-1. Then, the prepared sample was treated with osmotic stress in the same manner as in Example 1-2 and Example 1-3, and then a cambium-derived cell line was induced from the carrot.

Figure 6:
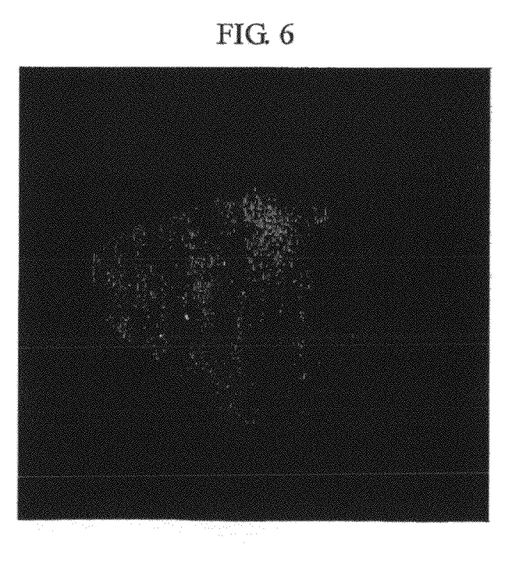
FIG. 6 shows that a homogeneous cell line derived from cambium was induced in a carrot root cambium-containing explant.

As a result, in the same manner as in Examples 1 and 2, it was observed that tissues other the cambium were necrotized and that the cambium-derived homogeneous cell line having the ability to divide was induced. FIG. 6 shows that the cambium-derived homogeneous cell line having the ability to divide was induced in the carrot.

Also, other plant hormone auxins, including IAA, IBA, picloram, 2,4-D, CPA and NAA, were used at the same concentration to examine the influence of the hormone used in induction medium. Table 8 shows results obtained when various kinds of auxins were used in the induction medium.

TABLE 8

Cell line induction patterns upon treatment of carrot with varying kinds of auxins at the same concentration

| | Kind of hormone | | | | | |
|---|---|---|---|---|---|---|
| | IAA | IBA | Picloram | CPA | 2,4-D | NAA |
| Reaction with respect to cambium | ++++ | ++++ | − | − | − | − |
| Others | | The homogeneous cell line was induced with respect to the cambium | The cell line was induced throughout the whole explant | | | The cell line was induced throughout the whole explant. With the passage of time, a root was induced around the cambium |

+: positive; and −: negative

As shown in Table 8, when IAA or IBA was used in induction medium, the homogeneous cell line was induced with respect to the cambium, whereas, when picloram, CPA, 2,4-D or NAA was used in induction medium, the cell line was induced throughout the whole explant rather than with respect to the cambium. Particularly, when NAA was used in induction medium, it was observed that, with the passage of time (after about 4 weeks), a root was induced and differentiated in the cambium. Thus, it was confirmed that a hormone used for the induction of the cambium-derived cell line is limited to IAA or IBA.

Example 4

Observation of Characteristics of Isolated Cell Line 4-1: Establishment of Long-Term Culture for Cambium-Derived Cell Line Among the ginseng cambium-derived homogeneous cell lines having the ability to divide, obtained in Example 1, white and friable cells having high growth rate were subcultured while replacing the medium with a fresh optimal growth medium (medium 3 of Table 7) at a 14-day interval. As a control group, a ginseng cotyledon-derived heterogeneous cell line was subcultured in an optimal growth medium while replacing the medium at a 28-day interval.

As a result, the white and friable cells of the cambium-derived homogeneous cell line continuously proliferated up to 11 months of the culture. Also, even when the cells were cultured for 11 months or more, the cells were stably maintained without changes in cell growth rate, growth pattern and aggregation degree and showed a growth rate which was about 400-fold higher than that of the ginseng cotyledon-derived heterogeneous cell line.

On the other hand, the ginseng cotyledon-derived heterogeneous cell line, which was a group of yellow, large and friable cells, was yellowish at the initial stage of culture while showing a tendency of 2-fold increase in cell population at a 4-week interval, and after 5 months of culture, the growth rate thereof showed to a tendency to decrease. Then, it showed a less than 1.5-fold increase in cell population, and in addition to yellow cells, white or light-gray watery cells, brown cells and the like appeared. Such cells no longer proliferated, remained intact and were dead with the induction of a large amount of brown material. Accordingly, when the ginseng cotyledon-derived heterogeneous cell line was cultured for 11 months, the growth rate thereof showed a tendency to decrease.

Figure 7:
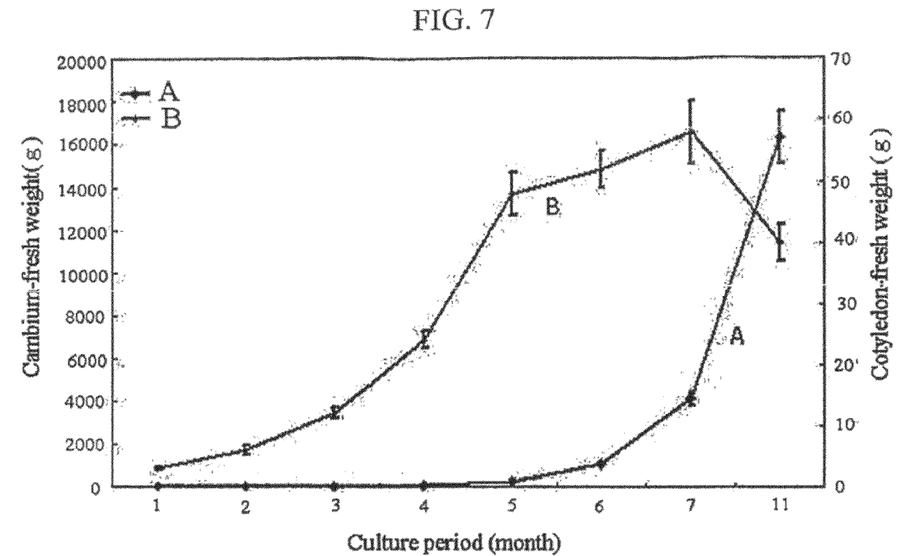
FIG. 7 shows growth curves of a ginseng cambium-derived cell line (A) and a ginseng cotyledon-derived cell line (B) according to the culture period.

FIG. 7 shows growth curves in long-term culture of the ginseng cambium-derived cell line (A) and the ginseng cotyledon-derived heterogeneous cell line.

4-2: Establishment of Cell Suspension Culture

The ginseng cambium- and true wild ginseng cambium-derived cell lines obtained in Examples 1 and 2 were placed in flasks containing a liquid medium shown in Table 9. Then, the cell lines in the flasks were cultured in a rotating shaker at 100 rpm in a dark condition at 25±1° C. Herein, the ginseng cambium- and true wild ginseng cambium-derived cell lines were cultured using 2,4-D, and the true wild ginseng adventitious root cambium-derived cell line was cultured using IBA. The subculture interval was set to 2 weeks, such that the cultured cells could always maintain high vitality in the exponential growth phase. Meanwhile, the ginseng cotyledon-derived callus (KCTC 10224), which was a heterogeneous cell line, was also cultured in medium 4 shown in Table 9 in order to compare with the inventive cambium-derived homogeneous cell lines having the ability to divide.

TABLE 9

Suspension culture medium (medium 4) for cambium-derived cell lines

| Component | Concentration and condition |
|---|---|
| Salt | Full strength MS |
| Sucrose | 3% (w/v) |
| 2,4-D(2,4-dichlorophenoxyacetic acid) or IBA | 2 mg/L |
| pH | 5.8 |

Figure 8:
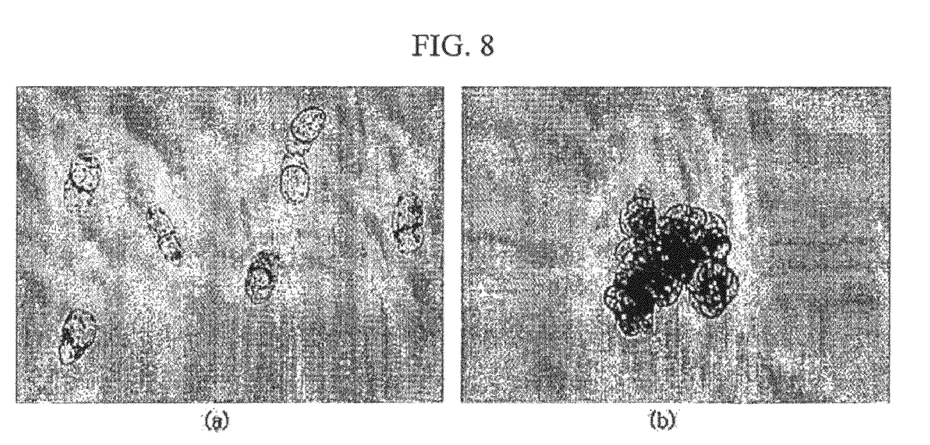
FIG. 8(a) is a microscopic image showing that a ginseng cambium-derived cell line is present in a single cell population.
FIG. 8(b) is a microscope showing that a heterogeneous cell line derived from the ginseng cotyledon is present in a large cell aggregation population.

The quantification of cell aggregation was observed under an optical microscope (biological microscope CX31, Olympus, Japan) and, as a result, it could be seen that, as shown in Table 10, the cambium-derived cell lines according to the present invention were present as single cells during suspension culture. However, it could be seen that more than 90% of the ginseng cotyledon-derived heterogeneous cell line was present as large cell aggregates, and less than 1% thereof was present as single cells. FIG. 8(a) is an optical microscopic image showing that the ginseng cambium-derived cell line was present in a single-cell population, FIG. 8(b) is a microscopic graph showing that the ginseng cotyledon-derived heterogeneous cell line is present as a large cell aggregate population.

TABLE 10

Cell aggregate type of cambium-derived cell lines during long-time culture

| Large cell aggregates | Moderate cell aggregates | Small cell aggregates | Single cell population | Explant source |
|---|---|---|---|---|
| 90% | 7% | 2% | 1% | cotyledon |
| 0 | 0 | 5% | 95% | ginseng cambium |
| 0 | 0 | 5% | 95% | True wild ginseng cambium (2,4-D treatment) |
| 5% | 10% | 25% | 60% | True wild ginseng cambium (IBA treatment) |

Large cell aggregates, size higher than $1.5 \times 10^3$ μm;
Moderate cell aggregates $1 \times 10^3$ μm;
Small cell aggregates $4 \times 10^2$ μm < size < $1 \times 10^3$ μm Meanwhile, when observed under a microscope, as can be seen in FIG. 4(c) or FIG. 5(c), the cambium-derived cell line according to the present invention had morphological characteristics of a number of vacuoles and was in an undifferentiated state. However, as shown in FIG. 4(d), the results of observation of the ginseng cotyledon-derived callus (KCTC 10224) showed that few or one big vacuole was observed.

4-3: Scale-Up Culture

In order to examine the possibility of scale-up culture, each of the ginseng cotyledon-derived heterogeneous callus and the cambium-derived cell lines obtained in Examples 2 and 3 was cultured in airlift bioreactor (Sung-Won Cytec, Korea) having an internal volume of 3 L. The medium used in the culture was a liquid medium shown in Table 9 and was maintained in a dark condition at 25

As a result, as shown in Table 11, the doubling time of the inventive cambium-derived homogeneous cell line having the ability to divide was 3-6 days, which did not differ from that in the flask or was rather shortened compared to that in the flask, whereas the doubling time of the ginseng cotyledon-derived heterogeneous cell line was 21 days in the flask and 28 days in the reactor. In other words, it was seen that, when cultured in the flask, the cambium-derived cell line according to the present invention showed about 3-5-fold higher growth rate compared to cell lines derived from other tissues, and when cultured in the reactor, the cambium-derived cell line according to the present invention showed 5-9-fold higher growth rate compared to cell lines derived from tissues other than the cambium. This is believed to be because cell viability of the heterogeneous cell line rapidly decreased due to growth ring production in the reactor, plant cell aggregation during culture, and the sensitivity of hard cell walls to shear stress.

The inventive cambium-derived cell line, which has the ability to divide and is homogeneous, formed a very small growth ring area in the bioreactor, and the ring on the inner wall was simply eliminated, when a simple stimulus was applied to the incubator to shake the medium. Also, it was shown that the inventive cell line had low aggregation and contained a large number of vacuoles, and thus had low sensitivity to shear stress, such that cell viability did not decrease. In other words, it was seen that the cambium-derived cell line according to the present invention had low sensitivity to shear stress resulting from shaking in the bioreactor for mass production, and thus could be produced rapidly in large amounts in the bioreactor. Accordingly, it could be seen that the cambium-derived cell line according to the present invention had 5-9-fold lower sensitivity to shear stress compared to cell lines derived from tissues other than the cambium.

TABLE 11

Doubling time of cambium-derived cell line and ginseng cotyledon-derived heterogeneous cell line in liquid suspension culture and bioreactor

| Explant source | Doubling time (day) | |
| --- | --- | --- |
| | flask | bioreactor |
| Cotyledon | 21 | 28 |
| Ginseng cambium | 5 | 3~4 |
| True wild ginseng cambium (2,4-D treatment) | 5 | 3~4 |
| True wild ginseng cambium (IBA treatment) | 7 | 5~6 |

Figure 9:
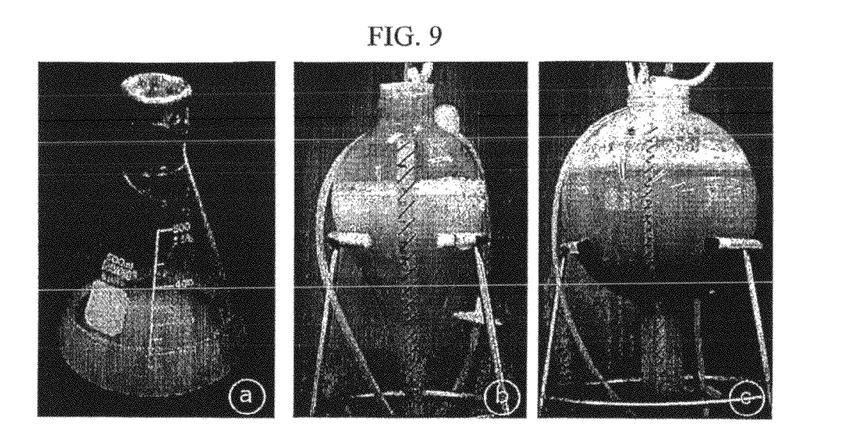
FIG. 9 depicts photographs of a flask culture (FIG. 9(a)), 3L bioreactor culture (FIGS. 9(b)) and 20 L bioreactor culture (FIG. 9(c)) of a cell line derived from the cambium of true wild ginseng.

Additionally, it was seen that the cambium-derived cell line according to the present invention could also be cultured in the airlift bioreactor (Sung-Won Cytec, Korea) having an internal volume of 20 L (FIG. 9), and thus could be cultured in large amounts.

4-4: Cryopreservation

Cryopreservation is a very ideal method of safely preserving a useful cell line selected for industrialization for a long period of time.

The method of safely preserving a useful cell line is as follows. The ginseng cotyledon-derived heterogeneous callus and the cambium-derived cell line were cryopreserved. A suspension culture was incubated for 6-8 days, and a cryopreservative was a medium containing 0.5M glycerol (DUCHEFA, The Netherlands), 0.5M DMSO (DUCHEFA, The Netherlands) and 1M sucrose (DUCHEFA, The Netherlands) and was transferred into a 5-ml cryovial (Duran, USA). The amount of cells inoculated into the cryopreservative was 200 mg/ml. The suspended cells treated with the cryopreservative were frozen by maintaining them in a freezer for 30 minutes, storing them in a deep freezer for 3 hours, and then soaking them in liquid nitrogen.

Then, for thawing, the cultured cells maintained in liquid nitrogen for 20 minutes or more were taken out, placed in a constant-temperature water bath at 40° C. and thawed for 1-2 minutes. For cell regrowth, the cell suspension was filtrated through a sterilized funnel and filter paper. The filtrated cells were applied on a solid growth medium including filter paper, and they were stabilized at room temperature for 30 minutes, and then transferred to a fresh solid growth medium.

As a result, the ginseng cotyledon-derived heterogeneous cell line did not regrow, whereas the cambium-derived cell line started to regrow and proliferate after 4 weeks and did not show a difference in growth rate between before and after cryopreservation.

4-5: Treatment with Elicitor

The true wild ginseng cambium-derived cell line, which has been suspension-cultured in 2,4-D-containing medium for 14 days as described in Example 4-2, was divided into three groups for experiments.

In other words, each of (1) the cell line (growth stage) suspension-cultured for 14 days, (2) a cell line (Elicitation 1), obtained by culturing the 14-day suspension-cultured cell line in a medium (containing sterile water, 3-5 wt % raw sugar and 100 µM methyl jasmonate) in a dark condition for 14 days, and (3) a cell line (Elicitation 2), obtained by culturing the 14-day suspension-cultured cell in a medium (containing 100 µM methyl jasmonate) in a dark condition for 14 days, was collected and subjected to the following test.

Example 5

Examination of Anti-Aging and Antioxidant Effect of Isolated Cell Line 5-1: Preparation of Extract of True Wild Ginseng Cambium-Derived Cell Line An extract was prepared from the cell line of Example 4-5 in the following manner. 500 g of each of a cell line (Wet) from which the culture medium has been removed and a freeze-dried cell line (Dry) was dissolved in 500 ml of DMSO at 50° C. for 6 hours with stirring. The resulting cell solution was centrifuged at 3,000 g for 10 minutes, and the supernatant was collected to obtain a distilled water-soluble material. The obtained DMSO-soluble material was concentrated using a rotary vacuum evaporator, and the concentrated sample was dried using a freeze drier, thus obtaining a DMSO extract.

5-2: Examination of Anti-Aging Effects of Culture Medium and Extract of True Wild Ginseng-Derived Cell Line: Examination of Effect of Inhibiting MMP-1 Expression Caused by UV Light When MMPs are increased due to exposure to UV light, the increased MMPs degrade skin collagen to form skin wrinkles. Thus, the following test was carried out in order to examine whether MMP-1 expression increased due to UV light is inhibited by an extract or culture medium of the true wild ginseng cambium-derived homogeneous cell line.

NHF (normal human fibroblast) cells used in the test were isolated from the fetal penis prepuce and cultured. The culture medium was prepared by adding 10% fetal bovine serum (FBS, Hyclone, Logan, Utah, USA), inactivated by heating at 56° C. for 30 minutes, 100 unit/ml of penicillin, 100 µg/ml of streptomycin and 300 µg/ml of glutamine to DMEM medium (Invitroge Gibco life tech. Vienna, Austriea). The cells were cultured in the medium in a 5% $CO_2$ incubator at a temperature of 37° C. and a humidity of 95% and subcultured at 3-4-day intervals, immediately before the cells were fused with each other.

NHF(p6) cells were dispensed into a 12-well plate at a density of 75,000 cells/well and starved for 24 hours. Then, the cells were radiated with 40 mJ of UVB and treated with varying concentrations of each sample for 48 hours. Then, an experiment was carried out using a kit (Amersham, RPN 2610). As a positive control group, 10 μM retinoic acid was used.

Elicitation 1 indicates a DMSO extract of the cell line of Example 5-3 treated with 3-5 wt % (g/L) of raw sugar and 100 μM of methyl jasmonate, Elicitation 2 indicates a DMSO extract of the cell line of Example 5-4 treated with 100 μM of methyl jasmonate, Growth indicates a DMSO extract of the 14-day suspension-cultured cell line (Growth stage) of Example 5-4, Wet indicates a DMSO extract of the cell line from which the culture medium has been removed, Dry indicates a DMSO extract of the freeze-dried cell line, and Media indicates the culture medium removed during the preparation of the cell line extract.

TABLE 12

Inhibitory effects of extract or culture medium of true wild ginseng cambium-derived homogeneous cell line on MMP-1 expression caused by UV light

| Sample | Step | Concentration (ppm or %) | % of control |
| --- | --- | --- | --- |
| No UV | | | 100 |
| Control UV | | | 230 |
| Retinoic acid | | 10 uM | 85 |
| Wet (ppm) | Elicitation 1 | 100 | 125 |
| | | 10 | 130 |
| | Elicitation 2 | 100 | 125 |
| | | 10 | 135 |
| | Growth | 100 | 140 |
| | | 10 | 160 |
| Dry (ppm) | Elicitation 1 | 50 | 120 |
| | | 10 | 140 |
| | Elicitation 2 | 50 | 135 |
| | | 10 | 180 |
| | Growth | 50 | 100 |
| | | 10 | 165 |
| Media (%) | Elicitation 1 | 1/10 | 60 |
| | | 1/20 | 130 |
| | Elicitation 2 | 1/10 | 60 |
| | | 1/20 | 200 |
| | Growth | 1/10 | 230 |
| | | 1/20 | 250 |

Figure 10:
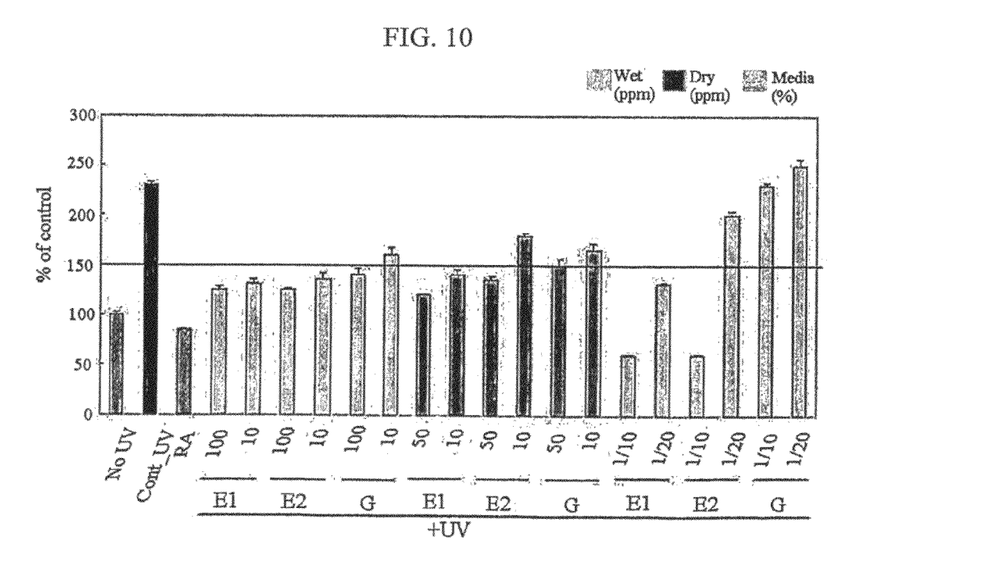
FIG. 10 is a graphic diagram showing whether MMP-1 expression, which was increased by ultraviolet ray (UVB) radiation, in normal human skin fibroblasts (NHF) treated with varying concentrations of a true wild ginseng cambium-derived homogeneous cell line extract or its culture and radiated with UVB, is inhibited by true wild ginseng cambium-derived homogeneous cell line extract or its culture.

As a result, as shown in Table 12 and FIG. 10, the cell line extract and culture medium according to the present invention effectively inhibited the expression of MMP-1 compared to the negative control group (Control UV), suggesting that they had the effects of preventing and reducing wrinkles. Particularly, when the NHF(p6) cells were treated with 0.1% of the cell line cultures of Elicitation 1, treated with raw sugar and methyl jasmonate, and Elicitation 2, treated only with methyl jasmonate, these cell line cultures medium showed a very excellent effect compared to retinoic acid known to have the strongest effect on wrinkle reduction among materials known in the prior art.

5-3: Examination of Antioxidant Effects of Culture Medium and Extract of True Wild Ginseng Cambium-Derived Cell Line: Examination of Inhibitory Effect on Active Oxygen Caused by UV Light In order to examine whether active oxygen, which were increased by UV light, is inhibited by the extract or culture medium of the true wild ginseng cambium-derived homogeneous cell line, HaCaT cells were dispensed into a 96-well black plate at a density of 30,000 cells/well and treated with varying concentrations of each of the samples for 3 hours. After 3 hours, the plate was washed once with HBSS, each well was treated with 50 μM DCF and incubated at 37° C. for 20 minutes. After the plate was washed twice with HBSS, the initial absorbance of the cells was measured using a luminator. The cells were radiated with 30 mJ of UVB, cultured at 37° C. for 2 hours, and then measured for absorbance. Control indicates a group not treated with the sample and UVB, and UVB indicates a group treated only with UVB without adding the sample.

TABLE 13

Inhibitory effects of extract or culture medium of true wild ginseng cambium-derived homogeneous cell line on active oxygen caused by UV light

| Sample | Step | Concentration (ppm or %) | % of control |
| --- | --- | --- | --- |
| Control | | | 100 |
| UVB | | | 140 |
| Wet (ppm) | Elicitation 1 | 100 | 80 |
| | | 10 | 170 |
| | Elicitation 2 | 100 | 140 |
| | | 10 | 135 |
| | Growth | 100 | 150 |
| | | 10 | 170 |
| Dry (ppm) | Elicitation 1 | 50 | 50 |
| | | 10 | 135 |
| | Elicitation 2 | 50 | 140 |
| | | 10 | 135 |
| | Growth | 50 | 105 |
| | | 10 | 145 |
| Media (%) | Elicitation 1 | 10 | 100 |
| | | 1 | 130 |
| | Elicitation 2 | 10 | 130 |
| | | 1 | 105 |
| | Growth | 10 | 110 |
| | | 1 | 120 |

Figure 11:
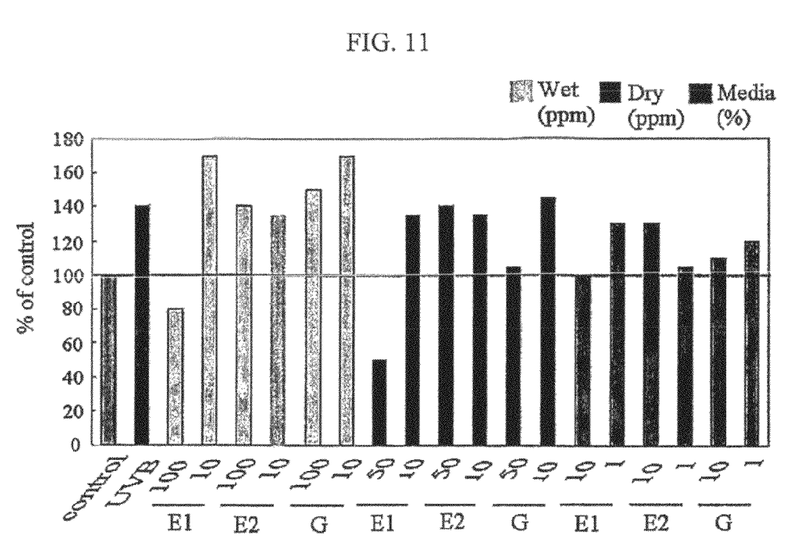
FIG. 11 is a graphic diagram showing whether an increase in active oxygen, caused by ultraviolet ray (UVB) radiation, in normal human skin fibroblasts (NHF) treated with varying concentrations of a true wild ginseng cambium-derived homogeneous cell line extract or its culture medium and radiated with UVB, is inhibited by the true wild ginseng cambium-derived homogeneous cell line extract or its culture.

As a result, as shown in Table 13 and FIG. 11, in the case where the inventive cell line from which the culture medium has been removed (Wet) was used and where the inventive freeze-dried cell line was used (Dry), the cell line extract of Elicitation 1 showed an excellent antioxidant effect. Then, Elicitation 2 and Growth stage showed similar antioxidant effects. Also, the group treated with 50 ppm of the freeze-dried cell line extract of Elicitation 1 showed the most excellent antioxidant effect.

5-4: Analysis of Ginsenoside Components

It is known that the ginsenoside components of true wild ginseng extract are effective in skin aging prevention and antioxidation. Thus, in order to examine whether the skin aging effects and antioxidant effects of the cell line extract and culture medium according to the present invention are attributable to the effects of such ginsenoside components, the content of ginsenosides was measured. Specifically, the true wild ginseng cambium-derived homogeneous cell line prepared in Example 2 and true wild ginseng were freeze-dried, and 20 mg of the freeze-dried cell line was extracted in 600 μl of methanol for 1 hour. The extract was centrifuged and the supernatant was collected. The content of ginsenosides in the isolated extract was measured using HPLC, and the measured content was shown in comparison with standard Re, Rb1, Rb2 and Rd. Also, the culture medium of Elicitation 1 was filtrated using a 0.2 μm syringe filter, and the content of ginsenosides therein was measured using HPLC. The measured content was shown in comparison with standard Re, Rb1, Rb2 and Rd.

TABLE 14

Comparison of ginsenoside content between true wild ginseng cambium-derived homogeneous cell line, culture medium and true wild ginseng

| | true wild ginseng cambium-derived cell line | | | Culture medium | True wild ginseng |
|---|---|---|---|---|---|
| | Growth | Elicitation 1 | Elicitation 2 | | |
| Ginsenoside (Rb1, Rb2, Rd, Re) | 0% | 0.003% | 0.018% | 0% | 3% |

As a result, as can be seen in Table 14, the cell line of Elicitation 2 showed the highest ginsenoside content, among the true wild ginseng cambium-derived homogeneous cell lines, but ginsenoside content of true wild ginseng extract, a control group, was still 167-fold higher than the ginsenoside content of true wild ginseng cambium-derived homogeneous cell line. Also, no ginsenoside was detected in the true wild ginseng cambium-derived cell line of growth stage or the cell line culture medium. This suggests that the skin aging-preventing and antioxidant effects of the cell line extract and culture medium according to the present invention are not attributable to ginsenosides and that the cell line isolated according to the method of the present invention contains active ingredients that differ from those of conventional true wild ginseng cells. Furthermore, the skin aging-preventing and antioxidant effects of the cell line extract and culture medium according to the present invention were very excellent even compared to retinoic acid known to have the strongest effect on wrinkle reduction among materials known in the prior art, suggesting that the cell line extract and culture medium according to the present invention have significantly high effects compared to those of conventional true wild ginseng extracts.

INDUSTRIAL APPLICABILITY

As described above, the inventive cell line derived from the cambium of an herbaceous plant having a storage root has an active cell division ability and is homogeneous. Also, it is stable during culture, because it has not undergone a dedifferentiation process. Thus, through the optimization of proliferation thereof, the cell line can be allowed to proliferate in a large amount within a short time. Accordingly, the inventive cell line derived from the cambium of an herbaceous plant having a storage root makes it possible to produce large amounts of useful plants which are difficult to cultivate outdoor due to various problems associated with the period of cultivation, the selection of cultivation land, cultivation cost and the like.

Moreover, the inventive cell line derived from the cambium of an herbaceous plant having a storage root shows an antioxidant effect of inhibiting active oxygen caused by exposure to UV light that is the major cause of skin aging and can effectively reduce or inhibit aging-related factors. Thus, the cambium-derived cell line of the present invention is useful for the prevention and inhibition of skin aging.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A method for isolating a cell line derived from the cambium of an herbaceous plant having a storage root, the method comprising:
    (a) obtaining storage root tissue of an herbaceous plant having a storage root, wherein the tissue comprises cambium;
    (b) treating the tissue such that differentiated, non-cambium cells lose the ability to divide, by subjecting the tissue to an agent which produces an osmotic stress;
    (c) inducing cambium cell proliferation by culturing the obtained cambium-containing storage root tissue in an induction medium comprising a cambium-division-specific hormone, wherein the cambium-division-specific hormone is indole-3-acetic acid (IAA), indole-3-butyric acid (IBA), or a combination thereof and;
    (d) collecting the induced cambium-derived cell line.

2. The method of claim 1, wherein the herbaceous plant is selected from the group consisting of *Codonopsis lanceolata, Ostericum koreanum, Platycodon grandiflorum, Pueraria thunbergiana, Aralia contonentalis, Ledebouriella seseloides, Angelica gigas*, carrot, sweet potato, Maca, and cassava.

3. A method for isolating a cell line derived from the cambium of a ginseng root, the method comprising:
    (a) obtaining root tissue of a ginseng plant, wherein the tissue comprises cambium;
    (b) treating the tissue such that differentiated, non-cambium cells lose the ability to divide, by subjecting the tissue to an agent which produces an osmotic stress;
    (c) inducing cambium cell proliferation by culturing the obtained cambium-containing root tissue in an induction medium comprising a cambium-division-specific hormone, wherein the cambium-division-specific hormone is indole-3-acetic acid (IAA), indole-3-butyric acid (IBA), or a combination thereof; and
    (d) collecting the induced cambium-derived cell line.

4. The method of claim 3, wherein the ginseng plant is selected from the group consisting of cultivated ginseng and true wild ginseng.

5. The method of claim 1, wherein said induction medium comprises IAA or IBA at a concentration of about 0.1 to about 5 mg/l.

6. The method of claim 1, wherein the treatment of step (b) comprises subjecting the tissue to an agent which produces osmotic stress wherein the agent is sucrose.

7. The method of claim 1, further comprising transferring the cambium-derived cell line to a maintenance medium which supports continued proliferation of said cambium-derived cell line.

8. The method of claim 7, wherein said maintenance medium comprises auxin.

9. The method of claim 8, wherein said maintenance medium comprises one or more of 2,4-dichlorophenoxyacetic acid (2,4-D), picloram, or IBA.

10. The method of claim 9, wherein said maintenance medium comprises 2,4-D, picloram or IBA at a concentration of about 1 to about 5 mg/L.

11. The method of claim 3, further comprising preserving said cambium-derived cell line by freezing, wherein said cambium-derived cell line can be thawed and recultured.

* * * * *